(12) United States Patent
Shelly et al.

(10) Patent No.: US 9,839,058 B2
(45) Date of Patent: Dec. 5, 2017

(54) MULTI FUNCTION DOCKING MODULE FOR A PRESSURE SUPPORT THERAPY SYSTEM

(71) Applicant: KONINKLIJKE PHILIPS N.V., Eindhoven (NL)

(72) Inventors: Benjamin Irwin Shelly, Pittsburgh, PA (US); Roger Wallace Strane, Irwin, PA (US)

(73) Assignee: Koninklijke Philips N.V., Eindhoven (NL)

( * ) Notice: Subject to any disclaimer, the term of this patent is extended or adjusted under 35 U.S.C. 154(b) by 139 days.

(21) Appl. No.: 14/443,430

(22) PCT Filed: Dec. 11, 2013

(86) PCT No.: PCT/IB2013/060803
§ 371 (c)(1),
(2) Date: May 18, 2015

(87) PCT Pub. No.: WO2014/097055
PCT Pub. Date: Jun. 26, 2014

(65) Prior Publication Data
US 2015/0296550 A1 Oct. 15, 2015

Related U.S. Application Data

(60) Provisional application No. 61/738,058, filed on Dec. 17, 2012.

(51) Int. Cl.
*H04W 76/02* (2009.01)
*A61M 16/00* (2006.01)
(Continued)

(52) U.S. Cl.
CPC ......... *H04W 76/023* (2013.01); *A61B 5/4836* (2013.01); *A61M 16/00* (2013.01);
(Continued)

(58) Field of Classification Search
CPC ..... A61M 16/06; H04W 40/00; H04W 74/00; H04W 80/00; H02J 50/10; B60L 11/1816; B60L 11/182; B60L 2230/16
(Continued)

(56) References Cited

U.S. PATENT DOCUMENTS 6,158,430 A 12/2000 Pfeiffer
8,156,937 B2 4/2012 Devries et al.
(Continued)

FOREIGN PATENT DOCUMENTS

CN 1907216 A 2/2007
CN 101810472 A 8/2010
(Continued)

OTHER PUBLICATIONS

"Architecture & Terminology Overview", Specification of the Bluetooth System, vol. 1, XP55180478A, 2014, pp. 1-18.
(Continued)

*Primary Examiner* — Paul Dinh (57) ABSTRACT

A charging and data transfer method for use in a pressure support system adapted to provide a regimen of respiratory therapy to a patient includes establishing a near-field wireless coupling interface between a pressure generating device base unit of the pressure support system and a wireless peripheral device (32) of the pressure support system, transferring energy from the pressure generating device base unit to the wireless peripheral device over the near-field wireless coupling interface and using the transferred energy in the wireless peripheral device to charge an energy storage device (72) of the wireless peripheral device, and transferring pairing information between the pressure generating device base unit and the wireless peripheral device over the near-field wireless coupling interface.

15 Claims, 6 Drawing Sheets

(51) Int. Cl.
  *A61M 16/06* (2006.01)
  *A61B 5/00* (2006.01)
  *H02J 7/02* (2016.01)
  *H04B 5/00* (2006.01)
  *A61M 16/20* (2006.01)
  *H02J 7/00* (2006.01)

(52) U.S. Cl.
  CPC ............ *A61M 16/06* (2013.01); *H02J 7/025* (2013.01); *H04B 5/0037* (2013.01); *A61B 5/6803* (2013.01); *A61B 2560/0456* (2013.01); *A61M 16/0069* (2014.02); *A61M 16/202* (2014.02); *A61M 2016/0027* (2013.01); *A61M 2016/0039* (2013.01); *A61M 2205/332* (2013.01); *A61M 2205/3569* (2013.01); *A61M 2205/3592* (2013.01); *A61M 2205/50* (2013.01); *A61M 2205/505* (2013.01); *A61M 2205/6054* (2013.01); *A61M 2205/8206* (2013.01); *A61M 2205/8243* (2013.01); *A61M 2205/8256* (2013.01); *A61M 2209/086* (2013.01); *A61M 2230/04* (2013.01); *A61M 2230/10* (2013.01); *A61M 2230/205* (2013.01); *A61M 2230/432* (2013.01); *A61M 2230/62* (2013.01); *A61M 2230/63* (2013.01); *H02J 2007/0096* (2013.01)

(58) Field of Classification Search
  USPC ........................................................ 320/108
  See application file for complete search history.

(56) References Cited

U.S. PATENT DOCUMENTS

| | | |
|---|---|---|
| 2005/0016540 A1 | 1/2005 | Jumpertz |
| 2006/0117859 A1 | 6/2006 | Liu et al. |
| 2007/0027388 A1 | 2/2007 | Chou |
| 2007/0299358 A1 | 12/2007 | Bertinetti et al. |
| 2008/0103407 A1* | 5/2008 | Bolea .................. A61N 1/0556 600/529 |
| 2009/0078257 A1* | 3/2009 | Bhat .................... A61B 5/0031 128/204.23 |
| 2010/0275919 A1 | 11/2010 | Sung |
| 2011/0066086 A1* | 3/2011 | Aarestad ................ H01P 5/222 601/11 |
| 2011/0306882 A1 | 12/2011 | Hannon et al. |
| 2012/0229272 A1 | 9/2012 | Jacob et al. |

FOREIGN PATENT DOCUMENTS

| | | |
|---|---|---|
| CN | 102054334 A | 5/2011 |
| CN | 102274035 A | 12/2011 |
| DE | 102007026565 A1 | 12/2007 |
| WO | 2010027282 A2 | 3/2010 |
| WO | 2011050059 A1 | 4/2011 |

OTHER PUBLICATIONS

"Bluetooth Secure Simple Pairing Using NFC (Application Document)", NFC Forum, 2011, pp. 1-32.

* cited by examiner (Prior Art)
FIG. 1

MULTI FUNCTION DOCKING MODULE FOR A PRESSURE SUPPORT THERAPY SYSTEM

CROSS-REFERENCE TO PRIOR APPLICATIONS

This application is the U.S. National Phase application under U.S.C. §371 of International Application Serial No. PCT/IB2013/060803, filed on Dec. 11, 2013, which claims the benefit of U.S. Application Ser. No. 61/738,058, filed on Dec. 17, 2012. These applications are hereby incorporated by reference herein.

BACKGROUND OF THE INVENTION

1. Field of the Invention

The present invention pertains to systems for treating conditions, such as sleep disordered breathing, using positive airway pressure (PAP) therapy, and, in particular, to a multi function docking module for a pressure support therapy system that enables a wireless peripheral component of such a system (e.g., a mask having a wireless pressure sensor) to be charged and wirelessly paired with a base unit of the pressure support therapy system through a near-field (e.g. inductive) coupling interface.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the pressure support device with the airway of the patient, so that a flow of breathing gas can be delivered from the pressure/flow generating device to the airway of the patient.

Pressure support therapy systems can be used with one or more electronic wireless peripheral devices that may require data transfer between the peripheral electronic device(s) and the base pressure generating device. For example, and without limitation, it is known to provide a wireless pressure sensor in a mask component of a pressure support therapy system, wherein the wireless pressure sensor is structured to wirelessly communicate pressure information measured by the sensor to the base pressure generating device using a short range wireless communications/data transfer protocol such as, without limitation, the Bluetooth® protocol.

As is known, wireless peripheral electronic devices often have rechargeable batteries for providing the on-board power that is required by the electronic components thereof. As a result, such wireless peripheral electronic devices need to be charged on a regular (e.g., daily) basis.

In addition, wireless communications/data transfer protocols are desirable and becoming less costly. Wireless data transfer protocols, especially Bluetooth®, typically require pairing between the two devices in question. As is known, such pairing typically requires user intervention.

Figure 1:
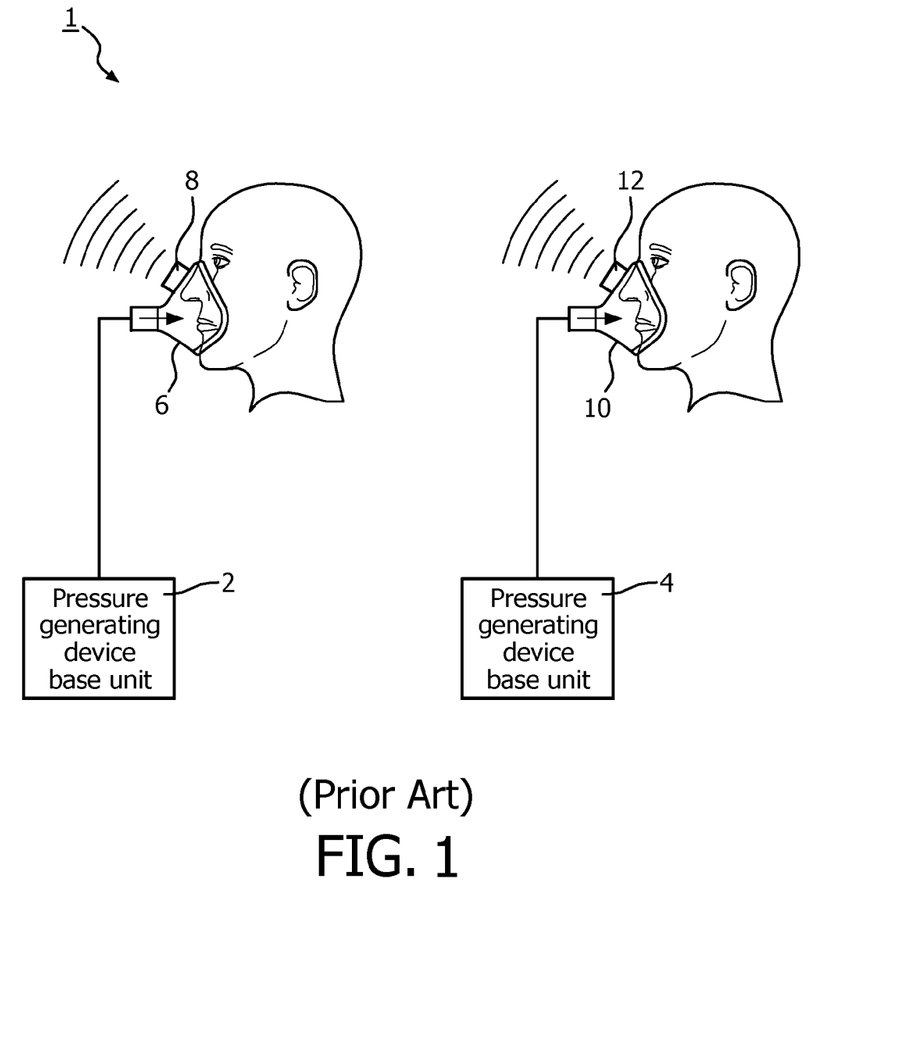
FIG. 1 is a schematic diagram of a prior art environment employing multiple pressure generating device base units and multiple patent interface peripheral devices.

While automatic pairing is technically feasible, methods to circumvent spurious pairing, for example between a base unit and peripherals that are not in use or between a base unit and peripherals that are in use but with another base unit (e.g. in a sleep lab environment or a home environment having multiple base units) are not adequately addressed in the prior art. Typical cases require the manual selection of a specific peripheral amongst a list of discovered peripherals. Such an environment 1 (e.g. in a sleep lab environment or a home environment having multiple base units) is shown schematically in FIG. 1. As seen in FIG. 1, environment 1 includes two pressure generating device base units 2 and 4, wherein pressure generating device base unit 2 is associated with mask 6 having peripheral device (e.g., wireless pressure sensor) 8 and pressure generating device base unit 4 is associated with mask 10 having peripheral device (e.g., wireless pressure sensor) 12. Thus, in environment 1, the two pressure generating device base units 2 and 4 are in proximity with the two peripheral devices 8 and 12, and both peripherals support wireless communication and are in use. Peripheral device 8 should be paired with pressure generating device base unit 2 and peripheral device 12 should be paired with pressure generating device base unit 4. However, there is no completely automated pairing solution available for this use case in the prior art. For example, a "just works" Secure Simple Pairing protocol may still require user intervention on the base unit, requiring selecting a given peripheral amongst a list of peripherals and having a unique code for a user to find and match amongst the list of peripherals.

SUMMARY OF THE INVENTION

In one embodiment, a charging and data transfer method for use in a pressure support system adapted to provide a regimen of respiratory therapy to a patient is provided that includes establishing a near-field wireless coupling interface between a pressure generating device base unit of the pressure support system and a wireless peripheral device of the pressure support system, transferring energy from the pressure generating device base unit to the wireless peripheral device over the near-field wireless coupling interface and using the transferred energy in the wireless peripheral device to charge an energy storage device of the wireless peripheral device, and transferring pairing information between the pressure generating device base unit and the wireless peripheral device over the near-field wireless coupling interface.

In another embodiment, a pressure support system adapted to provide a regimen of respiratory therapy to a patient is provided. The system includes a pressure generating device base unit having a docking module, and a wireless peripheral device, wherein the docking module is structured to receive the wireless peripheral device in a manner that establishes a near-field wireless coupling interface between the pressure generating device base unit and the wireless peripheral device, wherein the pressure generating base unit is structured to transfer energy to the wireless peripheral device over the near-field wireless coupling interface for charging an energy storage device of the wireless peripheral device, and wherein the pressure generating device base unit and the wireless peripheral device are structured to transfer pairing information over the near-field wireless coupling interface These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the terms "peripheral" and "peripheral device" shall mean any auxiliary electronic device that connects to and works with a base/host computing device in some way.

As used herein, the terms "pair", "pairing" or "paired" shall refer to a condition wherein two electronic devices capable of wireless communication using a predetermined common protocol, such as, without limitation, the Bluetooth® protocol, are communicably and wirelessly linked with one another under the predetermined common protocol.

As used herein, the term "pairing information" shall mean information that must be exchanged by two electronic devices in order for those devices to carry on an ongoing paired relationship with one another pursuant to a common protocol.

As used herein, the term "near-field" shall mean a region that is in proximity to an electromagnetic radiating structure, such as an antenna or coil, where the electric and magnetic fields do not have a plane-wave characteristic, but instead vary greatly from one point to another. Furthermore, the near-field can be subdivided into two regions which are commonly known as the reactive near-field and the radiating near-field. The reactive near-field is closest to the radiating structure and contains almost all of the stored energy, whereas the radiating near-field is where the radiation field is dominant over the reactive field but does not possess plane-wave characteristics and is complicated in structure. This is in contrast to the far-field, which is generally defined as the region where the electromagnetic field has a plane-wave characteristic, i.e., it has a uniform distribution of the electric and magnetic field strength in planes transverse to the direction of propagation.

As used herein, "near-field coupling" shall mean a technique wherein two devices are coupled to one another and transfer power and/or information within the near-field. One example of near-field coupling is near-field inductive coupling.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
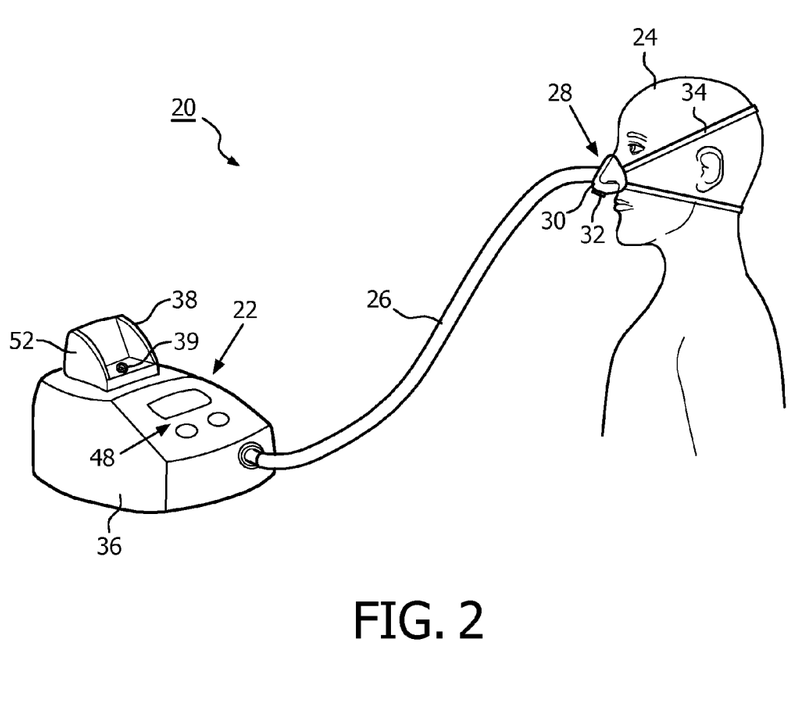
FIG. 2 is a schematic diagram of a system adapted to provide a regimen of respiratory therapy to a patient according to one exemplary embodiment of the invention.

FIG. 2 is a schematic diagram of a pressure support system 20 adapted to provide a regimen of respiratory therapy to a patient according to one exemplary embodiment of the invention. As seen in FIG. 2, pressure support system 20 includes a pressure generating device base unit 22 which generates a flow of breathing gas that is delivered to a patient 24 through a patient circuit that includes a delivery conduit 26 coupled to a patient interface device 28. In the exemplary embodiment, patient interface device 28 includes a mask component 30 having a wireless peripheral device 32 (comprising a pressure sensor) coupled thereto and a headgear component 34 for securing the patient interface device 28 to the head of patient 24.

Figure 4:
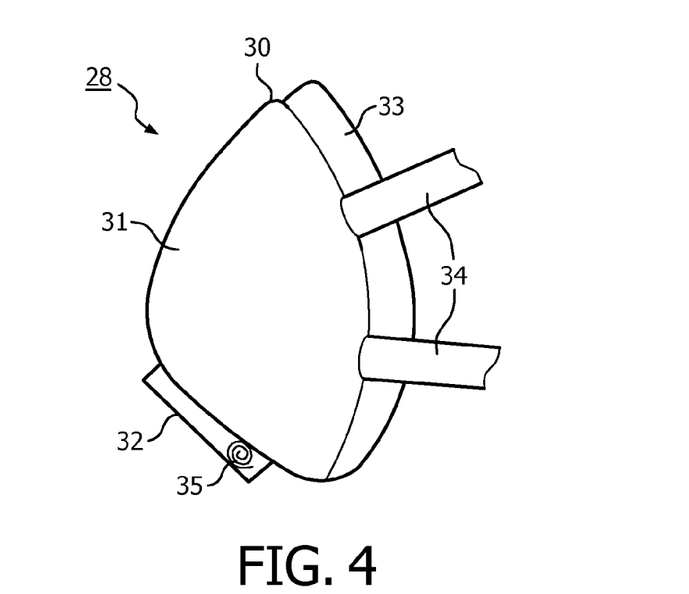
FIG. 4 is a side schematic view of a patient interface device forming a part of the system of FIG. 2 according to one exemplary, non-limiting embodiment.

In the illustrated exemplary embodiment shown in FIG. 2 and in FIG. 4, mask component 30 is a nasal mask that includes a rigid or semi-rigid shell 31 having a flexible cushion/sealing member 33 attached thereto. It is to be understood, however, that mask component 30 can take on other forms, such as a nasal/oral mask, a pillows style nasal cushion, a cradle style nasal cushion, a full face mask, or any other patient interface device that provides a suitable gas flow communicating function. Also in the illustrated exemplary embodiment, wireless peripheral device 32 is operatively coupled to shell 31 as shown schematically in FIGS. 2 and 4, although other positions are also possible. As seen in FIG. 4, wireless peripheral device 32 is provided with a coupling inductor/coil 35 (in the form of a spiral coil member in the illustrated embodiment, although other forms are also possible), the purpose of which is described in detail elsewhere herein.

In addition, as seen in FIG. 2, pressure generating device base unit 22 of the illustrated, exemplary embodiment includes a housing 36 and a docking module 38 that is an integral part of the housing 36. Docking module 38 is described in detail elsewhere herein and is structured to receive mask component 30 and provide both: (i) charging functionality for wireless peripheral device 32, and (ii) automatic wireless pairing functionality (by exchanging pairing information that is required under the appropriate wireless communications protocol, such as Bluetooth®) to enable wireless peripheral device 32 to be paired with pressure generating device base unit 22. In the exemplary embodiment, both of these functions are provided though an inductive coupling interface between wireless peripheral device 32 and docking module 38 that is described in detail herein. Thus, as seen in FIG. 2, docking module 38 is provided with a coupling inductor 39 (in the form of a spiral coil member in the illustrated embodiment, although other forms are also possible) in order to provide the inductive coupling interface between it and coupling inductor 35 of wireless peripheral device 32.

Figure 3:
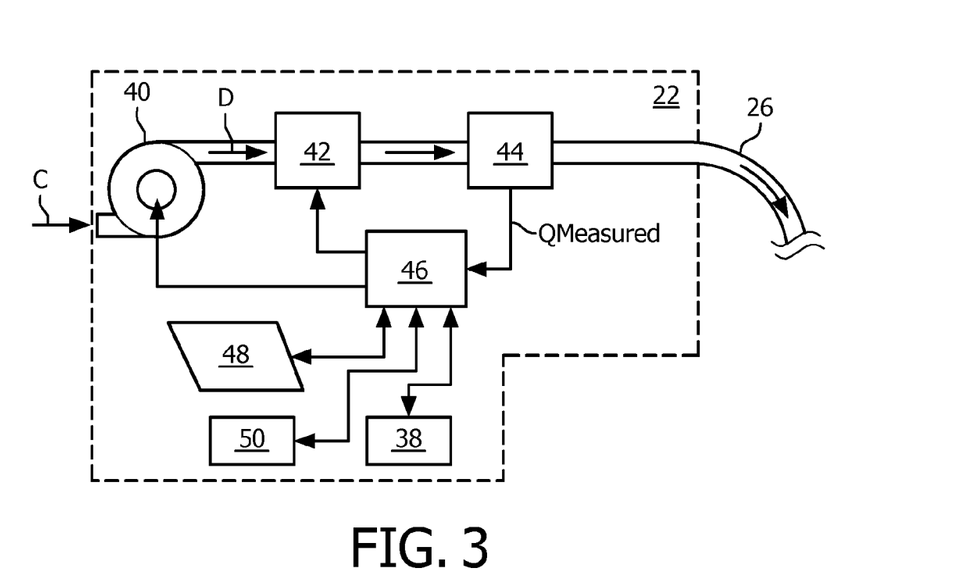
FIG. 3 is a schematic diagram of a pressure generating device base unit forming a part of the system of FIG. 2 according to one exemplary, non-limiting embodiment.

FIG. 3 is a schematic diagram of pressure generating device base unit 22 according to one exemplary, non-limiting embodiment. Pressure generating device base unit 24 includes a gas flow generator 40, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 40 generates a flow of breathing gas, such as air, oxygen, or a mixture thereof, for delivery to an airway of patient 24 at relatively higher and lower pressures, i.e., generally equal to or above ambient atmospheric pressure. The pressurized flow of breathing gas, generally indicated by arrow D from gas flow generator 40, is delivered via delivery conduit 26 to patient interface device 28.

Pressure support system 20 shown in FIG. 2 is what is known as a single-limb system, meaning that the patient circuit includes only delivery conduit 26 connecting patient 24 to pressure generating device base unit 22. As such, an exhaust vent (not shown) is provided in delivery conduit 26 for venting exhaled gasses from the system.

However, the present invention also contemplates that pressure support system 20 can be a two-limb system, having a delivery conduit and an exhaust conduit connected to patient 24. In a two-limb system (also referred to as a dual-limb system), the exhaust conduit carries exhaust gas from patient 24 and includes an exhaust valve at the end distal from patient 24. The exhaust valve in such an embodiment is typically actively controlled to maintain a desired level or pressure in the system, which is commonly known as positive end expiratory pressure (PEEP).

Referring again to FIG. 3, in the illustrated embodiment, pressure generating device base unit 22 includes a pressure controller in the form of a valve 42 provided in delivery conduit 26. Valve 42 controls the pressure of the flow of breathing gas from flow generator 40 delivered to patient 24. For present purposes, flow generator 40 and valve 42 are collectively referred to as a pressure generating system because they act in concert to control the pressure and/or flow of gas delivered to patient 24. However, it should be apparent that other techniques for controlling the pressure of the gas delivered to patient 24, such as varying the blower speed of flow generator 40, either alone or in combination with a pressure control valve, are contemplated by the present invention. Thus, valve 42 is optional depending on the technique used to control the pressure of the flow of breathing gas delivered to patient 24. If valve 42 is eliminated, the pressure generating system corresponds to flow generator 40 alone, and the pressure of gas in the patient circuit is controlled, for example, by controlling the motor speed of flow generator 40.

Pressure generating device base unit 22 further includes a flow sensor 44 that measures the flow of the breathing gas within delivery conduit 26. In the particular embodiment shown in FIG. 3, flow sensor 44 is interposed in line with delivery conduit 26, most preferably downstream of valve 42, although other positions are also possible. Flow sensor 44 generates a flow signal $Q_{MEASURED}$ that is provided to a controller 46 and is used by controller 46 to determine the rate of flow of gas at patient 24, referred to as $Q_{PATIENT}$. In addition, it should be noted that other techniques may be used to estimate flow. For example, flow may be estimated using motor parameters (e.g. motor current). Also, most modern pressure support system implementations include pressure sensors, which may be used to control the pressure at the outlet of the device (and, by extension, the pressure at the patient) as well as to perform other monitoring tasks (e.g. monitor acoustic signal for snoring).

Controller 46 includes a processing unit, such as, for example, a microprocessor, a microcontroller or some other suitable processing device, and a memory (that is provided as part of the processing unit or that is operatively coupled to the processing unit) that provides a tangible storage medium for data and software routines executable by the processing unit for controlling the operation of pressure support system 20 (e.g., as described herein for providing the dual charging/automatic pairing functionality of docking module 38). An input/output device 48 (also shown schematically in FIG. 2 as a display and a number of button members) is provided for setting various parameters used by pressure support system 20, as well as for displaying and outputting information and data to a user, such as a clinician or caregiver.

As seen in FIG. 3, pressure generating device base unit 22 in the exemplary embodiment also includes a short range wireless communications module 50 which is operatively coupled to controller 46. In the exemplary embodiment, short range wireless communications module 50 is a module that is structured and configured to enable pressure generating device base unit 22 to communicate with other, similarly equipped electronic devices (e.g., wireless peripheral device 32 coupled to mask component 30 as described herein) over a short range wireless network. In the exemplary embodiment, short range wireless communications module 50 is a Bluetooth® module that is structured and configured to enable pressure generating device base unit 22 to communicate with other devices over an ad hoc Bluetooth® network. In addition, short range wireless communications module 50 may be incorporated within pressure generating device base unit 22, or may be a module that is selectively connectable to pressure generating device base unit 22 via a USB port or other suitable connection.

Finally, as noted above, pressure generating device base unit 22 includes docking module 38 that is structured to provide both: (i) charging functionality for wireless peripheral device 32, and (ii) automatic wireless pairing functionality to enable wireless peripheral device 32 to be paired with pressure generating device base unit 22. In the exemplary embodiment shown in FIG. 2 and FIG. 5, docking module 38 is provided as an integral part of housing 36 of pressure generating device base unit 22, and includes a housing 52 that is shaped to receive and hold mask component 30 (and in particular shell 31) in a manner that positions coupling inductor 35 of wireless peripheral device 32 in close proximity to coupling inductor 39 of docking module 38 such that coupling inductor 35 will be within the near-field of coupling inductor 39 (in one example implementation, a pressure sensor module is provided in the dock). As described in detail elsewhere herein, this allows wireless peripheral device 32 to be charged by pressure generating device base unit 22 and to exchange pairing information with pressure generating device base unit 22 through the inductive coupling interface that is created between coupling inductor 35 and coupling inductor 39. In one particular exemplary embodiment, housing 52 may have one or more of a tray-like shape, a hanging feature, a magnetic feature, a clip, a strap and/or another feature to receive either part or all of mask component 30 (or any other structure to which wireless peripheral device 32 is attached) to help secure/locate wireless peripheral device 32 on docking module 38.

Figure 6:
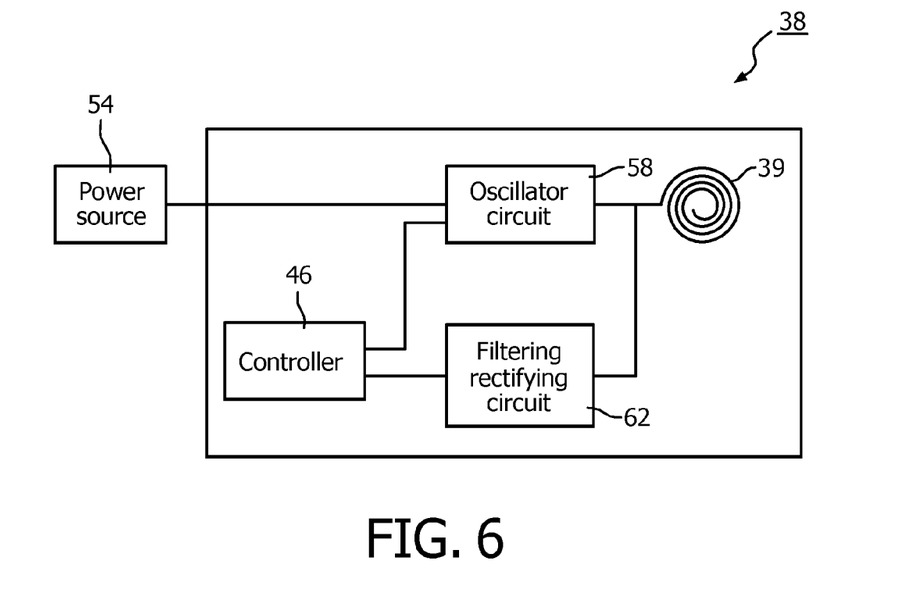
FIG. 6 is a schematic diagram showing selected components of a docking module of the pressure generating device base unit of FIG. 2 according to one particular, non-limiting exemplary embodiment.

FIG. 6 is a schematic diagram showing selected components of docking module 38 according to one particular, non-limiting exemplary embodiment. As seen in FIG. 6, docking module 38 is operatively coupled to a power source 54 within pressure generating device base unit 22 (e.g., provided from an AC outlet to which pressure generating device base unit 22 is coupled) and to controller 46. Docking module 38 includes an oscillator circuit 58 that is coupled to the output of power source 54. The output of oscillator circuit 58 is coupled to coupling inductor 39. In addition, docking module 38 further includes a controller 46 that is coupled to oscillator circuit 58 to enable control of both power and data. Coupling inductor 39 is also coupled to the input of a filtering and rectifying circuit 62, the output of which is coupled to controller 46.

Figure 7:
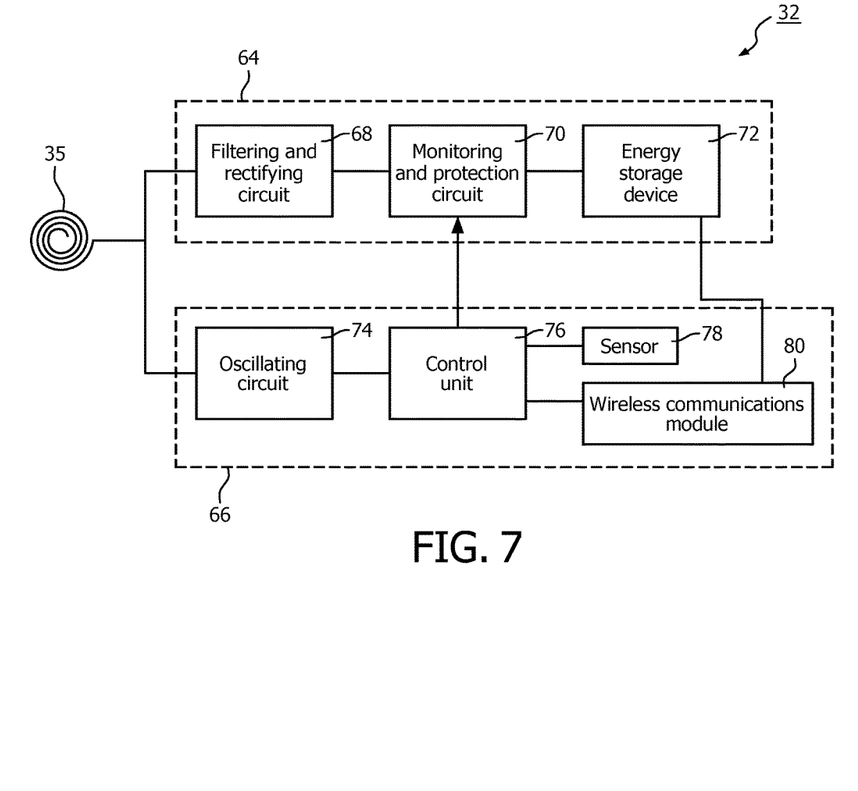
FIG. 7 is a schematic diagram showing selected components of a wireless peripheral device forming a part of the system of FIG. 2 according to one exemplary, non-limiting embodiment.

FIG. 7 is a schematic diagram showing selected components of wireless peripheral device 32 according to one particular, non-limiting exemplary embodiment. As seen in FIG. 7, wireless peripheral device 32 includes a charging/power circuit 64 and a data circuit 66, both of which are operatively coupled to coupling inductor 35. Charging/power circuit 64 includes a filtering and rectifying circuit 68, a monitoring and protection circuit 70, and an energy storage device 72 (e.g., without limitation, a rechargeable battery, such as Li ion battery, or a supercapacitor). Data circuit 66 includes an oscillating circuit 74, a control unit 76 coupled to oscillating circuit 74, a sensor (e.g., without limitation, a pressure sensor) 78 coupled to control unit 76, and a short range wireless communications module 80 coupled to control unit 76. Control unit 76 includes a processing unit, such as, for example, a microprocessor, a microcontroller or some other suitable processing device, and a memory (that is provided as part of the processing unit or that is operatively coupled to the processing unit) that provides a tangible storage medium for data and software routines executable by the processing unit for controlling the operation of wireless peripheral device 32. In the exemplary embodiment, short range wireless communications module 80 is a Bluetooth® module.

The operation of docking module 38 in conjunction with wireless peripheral device 32 being in a docked state (FIG. 5) will now be described. AC source 54 provides an AC voltage to rectifying circuit 56, which rectifies that voltage into a DC signal. That DC signal is used to drive power oscillator circuit 58. In response, power oscillator circuit creates an AC signal having a first frequency. That AC signal is provided to coupling inductor 39, and in response, coupling inductor 39 will radiate AC energy in the near-field of coupling inductor 39. As described elsewhere herein, in the docked state of FIG. 5, coupling inductor 35 of wireless peripheral device 32 will be within the near-field of coupling inductor 39, and a result, an AC signal will be induced in coupling inductor 35. That AC signal is provided to filtering and rectifying circuit 68 and monitoring and protection circuit 70, which together generate and ensure that a proper DC signal is provided to rechargeable battery 72 for charging rechargeable battery 72. Thus, when wireless peripheral device 32 is in the docked state of FIG. 5, rechargeable battery 72 will be charged through the inductive coupling interface between coupling inductor 39 and coupling inductor 35.

Figure 5:
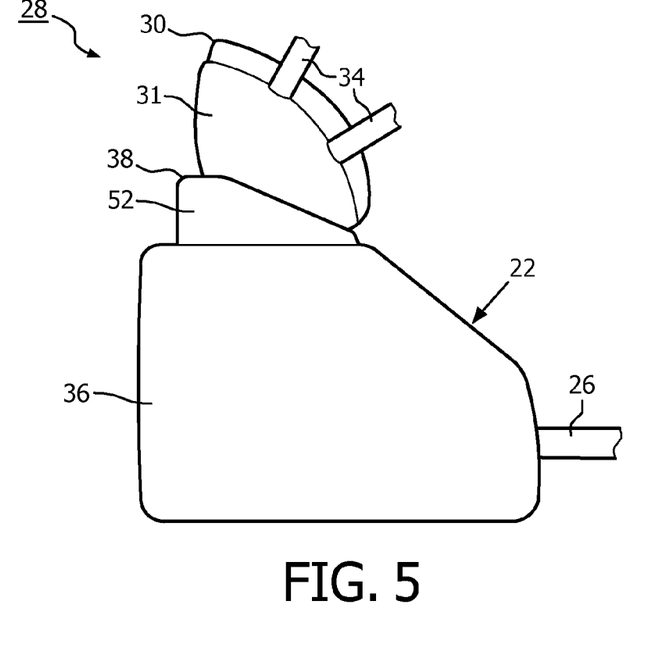
FIG. 5 is a side schematic view showing the patient interface device of FIG. 4 docked with pressure generating device base unit of FIG. 2 according to one exemplary, non-limiting embodiment.

In addition, as will be appreciated upon review of FIGS. 6 and 7, when wireless peripheral device 32 is in the docked state of FIG. 5, controller 46 of pressure generating device base unit 22 will be able to electronically communicate with control unit 76 of wireless peripheral device 32 (i.e., data may be transferred between the two devices) through the inductive coupling interface between coupling inductor 39 and coupling inductor 35 at the same time that rechargeable battery 72 is being charged. In the exemplary embodiment, a second AC frequency different than the first frequency (described above in connection with the charging function) will be used for this data transfer. Thus, in the configuration of the present invention, one or more of the following types of data (among others) may be transferred between pressure generating device base unit 22 and wireless peripheral device 32 over the inductive coupling interface: (i) pairing information for causing pressure generating device base unit 22 and wireless peripheral device 32 to be paired with one another using the appropriate wireless protocol (Bluetooth® in the present example so that pressure generating device base unit 22 and wireless peripheral device 32 can communicate using short range wireless communications modules 50 and 80 when wireless peripheral device 32 is removed from docking module 38), (ii) identifying information that identifies wireless peripheral device 32 by type (e.g., generally as a component of a pressure support system and/or more specifically as a particular type of pressure support system component, such as a mask), (iii) mask characterizing information (for example, the expected pressure drop over the peripheral or an expected range of pressure drops over the peripheral, or any other characteristic of the mask that may be interesting for the base unit to know, such as strap setup so the base unit device can provide fitting instructions, expected lifespan so the base unit device can provide replacement reminders, color so the base unit device GUI can match colors, etc.), (iv) degree of charge information indicating the current charge level of rechargeable battery 72 (so that, for example, that information can be displayed on input/output device 48), and (v) information used to modify control of either pressure generating device base unit 22 or wireless peripheral device 32 (for example, the base unit pressure generating device may use characterizing information to control the outlet pressure, or the peripheral device may control the transmission data rate).

In one particular embodiment, controller 46 of pressure generating device base unit 22 is programmed with one or more software routines that control operation of pressure generating device base unit 22 such that pressure generating device base unit 22 will only be permitted to establish a pairing relationship with a peripheral device that has identified itself as a pressure support system component if the pairing information is transferred between the two devices using an inductive coupling connection through coupling inductor 39. Thus, it is only when the pairing information is transferred between a peripheral device that has identified itself as a pressure support system component (e.g., a mask) pressure generating device base unit 22 using an inductive coupling connection through coupling inductor 39 that the pairing relationship will be permitted/established. As will be appreciated, in the illustrated embodiment, this will occur when a peripheral device, such as wireless peripheral device 32, is in the docked state of FIG. 5 and the pairing information is transferred between the two devices through the inductive coupling interface between coupling inductor 39 and, for example, coupling inductor 35. This feature will thus help to reduce or eliminate the problem of spurious pairing with peripheral device components in the environment of pressure generating device base unit 22 by ensuring that pairing only occurs with those peripheral devices that have been docked with pressure generating device base unit 22 (i.e., brought within the near-field of docking module 38). In another implementation, the pairing (or communication) information will be passed to the pressure generating device base unit 22 by the wireless peripheral device 32 through the inductive coupling interface and the communication relationship/channel will be opened while the wireless peripheral device 32 is on the charging dock. That connection will be maintained once the wireless peripheral device 32 is removed from the charging dock and the pressure generating device base unit 22 will not pair/communicate with another similar peripheral unless that first communication is stopped.

Figure 8:
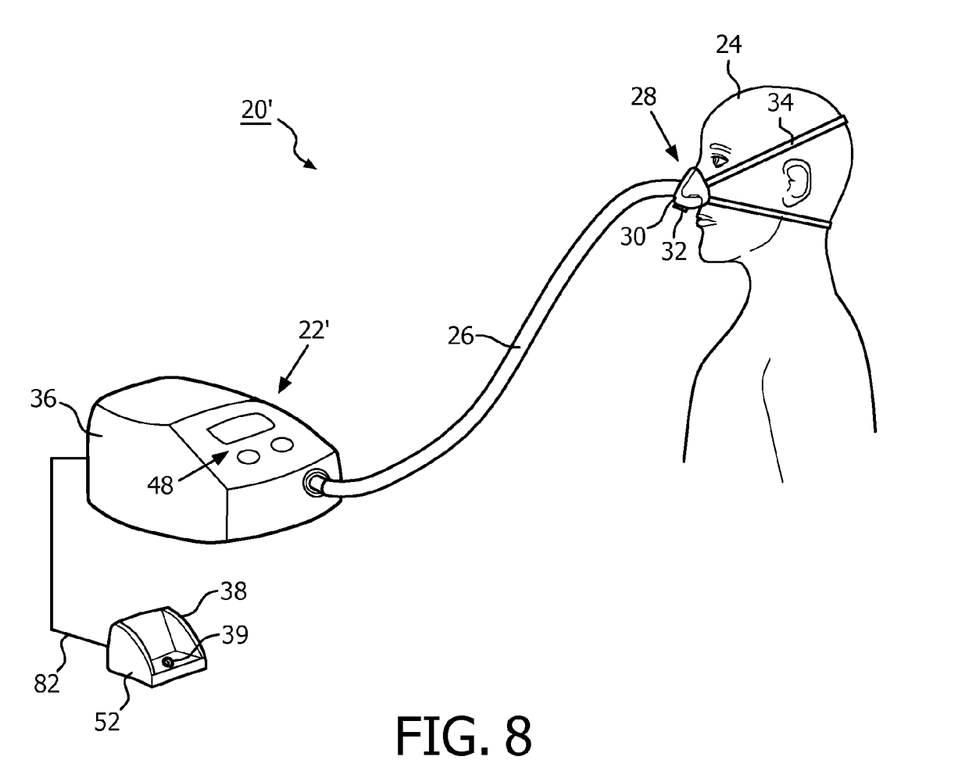
FIG. 8 is a schematic diagram of a system adapted to provide a regimen of respiratory therapy to a patient according to an alternative exemplary embodiment of the invention

FIG. 8 is a schematic diagram of a pressure generating system 20' adapted to provide a regimen of respiratory therapy to a patient according to an alternative exemplary embodiment of the invention. Pressure generating system 20' is similar to pressure generating system 20 shown in FIG. 2, and like components are labeled with like reference numerals. However, pressure generating system 20' includes a pressure generating device base unit 22' that, while similar to pressure generating device base unit 22 in that it generates a flow of breathing gas that is delivered to patient 24 through a patient circuit that includes delivery conduit 26 coupled to a patient interface device 28, is different in that is does not include an integrated docking module 38. Instead, as seen in FIG. 8, docketing module 38 forms part of pressure generating device base unit 22' by being selectively coupleable to the housing 36 of pressure generating device base unit 22' (and the internal components thereof) by a wired connection 82, which may be, for example and without limitation, a USB connection or any other type of suitable electronic connection. Otherwise, the functioning of pressure generating system 20' is the same as the functioning of pressure generating system 20.

The exemplary embodiments described herein include wireless peripheral device 32 in the form of a pressure sensor coupled to a mask. It will be understood, however, that wireless peripheral device 32 may be other types of peripheral devices and/or may be coupled to another part of pressure support system 20, such as, without limitation, any sensors suitable for use with CPAP systems ($SpO_2$, EEG, ECG, capnography, accelerometer, body position, etc.).

Furthermore, in the exemplary embodiments, both charging functionality and pairing information transfer functionality are provided through a near-field inductive coupling interface. It will be understood, however, that the present invention contemplates that charging functionality and pairing information transfer functionality can be provided through other types of near-field coupling interfaces, such as a capacitive coupling near-field interface, wherein power and information are transferred in between a base unit device and a peripheral device in the near-field of the base unit.

In a further alternative embodiment, pressure generating device base unit 22 may also be further structured to support wired charging of wireless peripheral device 32 or another peripheral device such as a smartphone using a suitable wired charging connector (e.g., without limitation, a USB connector or a, iPhone® or other smartphone dock connector). In such a configuration, a smartphone can be charged (using the wired connection or the inductive coupling interface described herein for a properly equipped smartphone) overnight while patient interface device 28 having wireless peripheral device 32 is in use. In such capacity, the smartphone can, for example, serve as an alarm clock as well as maintain data connectivity for software applications of pressure generating device base unit 22. During the day, while the smartphone is being used by the patient, wireless peripheral device 32 can be docked and charged as described herein. In addition, in such a configuration, the smartphone can be in electronic communication with controller 46 of pressure generating device base unit 22 using either the wired connection just described or the inductive coupling interface described herein. Such docking of the smartphone can cause automatic launching of a preferred application in the smartphone, such as, without limitation, the SleepMapper application, provided by the assignee of the preen invention, that provides information about the patient's PAP usage, or any other application that provides information about a CPAP device or usage thereof. Also, when so docked (or when recently docked), the smartphone can serve as a control mechanism and/or a real time display for pressure generating device base unit 22 (with data being provided through the wired connection just described, the inductive coupling interface described herein, or through a Bluetooth® or another short range wireless connection). Desirable display and control characteristics are known to those skilled in the art.

In addition, in still another embodiment, docking with a given peripheral device (e.g., wireless peripheral device 32 or a smartphone) as described herein can unlock advanced controls and/or advanced features of pressure generating device base unit 22 (e.g. allow BiPAP, Flex, EPR, etc.).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A charging and data transfer method for use in a pressure support system adapted to provide a regimen of respiratory therapy to a patient, comprising:
   establishing a near-field wireless coupling interface between a pressure generating device base unit of the pressure support system and a wireless peripheral device of the pressure support system, wherein the pressure generating device base unit and the wireless peripheral device are structured to wirelessly communicate with one another over a wireless communication channel separate and distinct from the near-field wireless coupling interface according to a predetermined common protocol, wherein the predetermined common protocol requires the pressure generating device base unit and the wireless peripheral device to be paired with one another by exchanging pairing information according to the predetermined common protocol before the pressure generating device base unit and the wireless peripheral device wirelessly communicate with one another on an ongoing basis over the wireless communication channel;
   transferring energy from the pressure generating device base unit to the wireless peripheral device over the near-field wireless coupling interface and using the transferred energy in the wireless peripheral device to charge an energy storage device of the wireless peripheral device; and
   transferring the pairing information between the pressure generating device base unit and the wireless peripheral device over the near-field wireless coupling interface.

2. The method according to claim 1, wherein near-field wireless coupling interface is an inductive coupling interface, wherein the pressure generating device base unit comprises a docking module having a first coupling coil, wherein the wireless peripheral device comprises a second coupling coil, and wherein the establishing step comprises receiving the wireless peripheral device in the docking module in a manner that establishes the inductive coupling interface between the first coupling coil and the second coupling coil.

3. The method according to claim 2, wherein the docking module is an integral part of a housing of the pressure generating device base unit.

4. The method according to claim 2, wherein the docking module is selectively coupleable to a housing of the pressure generating device base unit.

5. The method according to claim 1, wherein wireless peripheral device is part of a patient interface device of the pressure support system.

6. The method according to claim 1, further comprising pairing the pressure generating device base unit with the wireless peripheral device according to the predetermined common protocol following the step of transferring the pairing information, wherein the pairing is enabled based on the pairing information.

7. A pressure support system adapted to provide a regimen of respiratory therapy to a patient, comprising:
   a pressure generating device base unit having a docking module; and
   a wireless peripheral device;
   wherein the docking module is structured to receive the wireless peripheral device in a manner that establishes a near-field wireless coupling interface between the pressure generating device base unit and the wireless peripheral device, wherein the pressure generating base unit is structured to transfer energy to the wireless peripheral device over the near-field wireless coupling interface for charging an energy storage device of the wireless peripheral device, wherein the pressure generating device base unit and the wireless peripheral device are structured to wirelessly communicate with one another over a wireless communication channel separate and distinct from the near-field wireless coupling interface according to a predetermined common protocol, wherein the predetermined common protocol requires the pressure generating device base unit and the wireless peripheral device to be paired with one another by exchanging pairing information according to the predetermined common protocol before the pressure generating device base unit and the wireless peripheral device may wirelessly communicate with one another on an ongoing basis over the wireless communication channel, wherein the pressure generating device base unit and the wireless peripheral device are structured to transfer the pairing information over the near-field wireless coupling interface, wherein the pressure generating device base unit includes a controller storing software routines in a non-transitory computer readable medium that are executable by the controller, and wherein the software routines are for controlling operation of the pressure support system to cause the pressure generating device base unit to be automatically paired with the wireless peripheral device over the wireless communication channel by transferring the pairing information over the near-field wireless coupling interface when the wireless peripheral device is docked in the docking module and the near-field wireless coupling interface is established.

8. The pressure support system according to claim 7, wherein the pressure generating device base unit and the wireless peripheral device are structured to transfer the pairing information over the near-field wireless coupling interface while the energy is being transferred from the pressure generating device base unit to the wireless peripheral device over the near-field wireless coupling interface.

9. The pressure support system according to claim 7, wherein near-field wireless coupling interface is an inductive coupling interface.

10. The pressure support system according to claim 9, wherein the docking module has a first coupling coil, wherein the wireless peripheral device has a second coupling coil, and wherein the docking module is structured to receive the wireless peripheral device in a manner that establishes the inductive coupling interface between the first coupling coil and the second coupling coil.

11. The pressure support system according to claim 7, wherein the docking module is an integral part of a housing of the pressure generating device base unit.

12. The pressure support system according to claim 7, wherein the docking module is selectively coupleable to a housing of the pressure generating device base unit.

13. The pressure support system according to claim 7, wherein wireless peripheral device is part of a patient interface device of the pressure support system.

14. The pressure support system according to claim 7, wherein the wireless peripheral device comprises a sensor.

15. The pressure support system according to claim 7, wherein the pressure generating device base unit is structured to permit pairing with peripheral devices only in response to associated pairing information being transferred over the near-field wireless coupling interface.

* * * * *